United States Patent [19]
Wall et al.

[11] 4,169,961
[45] Oct. 2, 1979

[54] ALCOHOL PRODUCTION

[75] Inventors: Robert G. Wall, Pinole; John B. Wilkes, Richmond; Shigeto Suzuki, San Francisco, all of Calif.

[73] Assignee: Chevron Research Company, San Francisco, Calif.

[21] Appl. No.: 814,586

[22] Filed: Jul. 11, 1977

Related U.S. Application Data

[63] Continuation-in-part of Ser. No. 665,749, Mar. 11, 1976, abandoned, which is a continuation of Ser. No. 427,176, Dec. 21, 1973, abandoned.

[51] Int. Cl.$^2$ ............................................. C07C 31/20
[52] U.S. Cl. ............................................ 568/857
[58] Field of Search ...................... 260/635 R; 568/857

[56] References Cited

U.S. PATENT DOCUMENTS

| | | | |
|---|---|---|---|
| 2,868,846 | 1/1959 | Lawlor et al. | 260/633 |
| 3,574,773 | 4/1971 | Mueller et al. | 260/638 R |
| 3,692,848 | 9/1972 | Mueller et al. | 260/635 R |

*Primary Examiner*—Joseph E. Evans
*Attorney, Agent, or Firm*—D. A. Newell; John Stoner, Jr.; A. T. Bertolli

[57] ABSTRACT

An alkenediol is produced from an alkenol by contacting the alkenol with formaldehyde at a pH maintained between about 4 and 7. Preferably this pH range is maintained by adding a buffering agent composed of a weak acid and the salt of a weak acid. Particularly advantageous buffering agents are the lower organic polycarboxylic acids with disodium or dipotassium hydrogen phosphate and sodium or potassium dihydrogen phosphate with disodium or dipotassium hydrogen phosphate.

9 Claims, 1 Drawing Figure

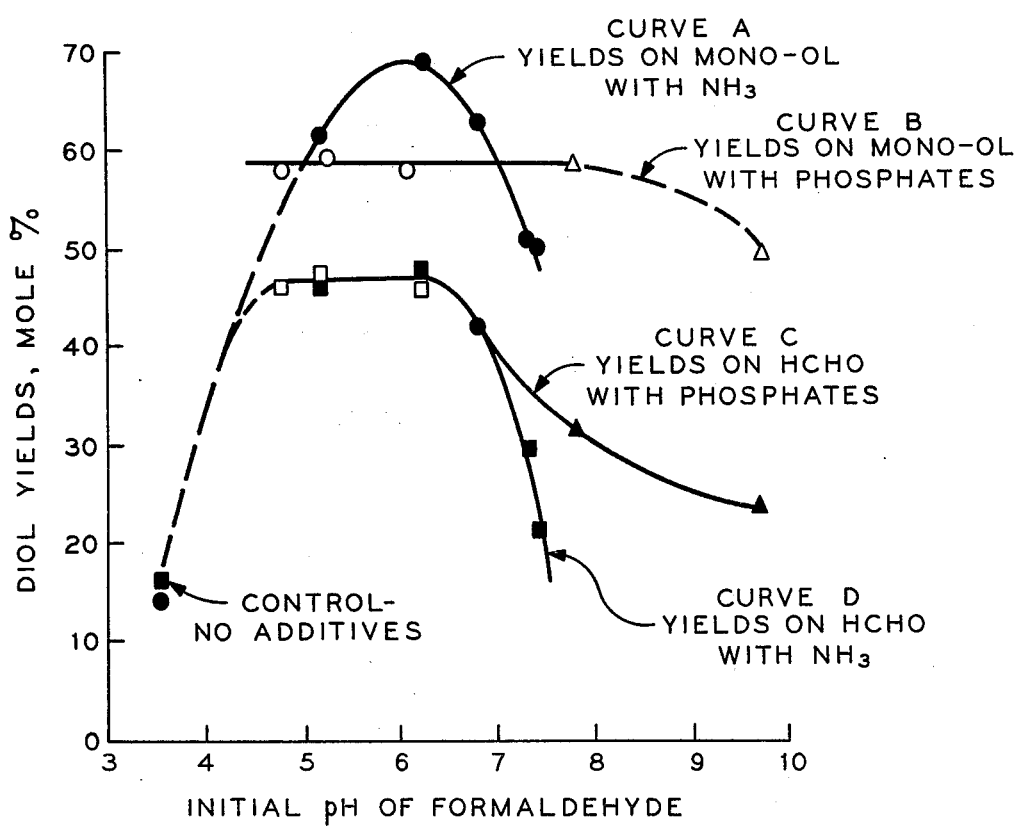

ALCOHOL PRODUCTION

CROSS-REFERENCE TO RELATED APPLICATIONS

This application is a continuation-in-part application of Ser. No. 665,749, filed Mar. 11, 1976, now abandoned, which in turn is a continuation application of Ser. No. 427,176, filed Dec. 21, 1973, now abandoned.

This application is related to commonly assigned application Ser. No. 379,511, filed July 16, 1973, the disclosure of which application is incorporated herein by reference. Ser. No. 379,511 has been abandoned in favor of Ser. No. 458,625, filed Apr. 8, 1974, which in turn has been abandoned in favor of Ser. No. 616,794, filed Sept. 25, 1975 which in turn has been abandoned in favor of Ser. No. 758,727, filed Jan. 12, 1977.

BACKGROUND OF THE INVENTION

The present invention relates to production of alkenediols by reaction of an alkenol with aqueous formaldehyde.

The alkenediols which are produced can be hydrogenated to alkanediols, which are in general useful in known processes for the production of polymers, resins, plasticizers and synthetic lubricants. Also, citric acid and other tertiary hydroxy polybasic acids can be produced from alkenediols containing methylene groups, as taught in Belgian Pat. Nos. 784,238 and 792,076.

U.S. Pat. No. 3,692,848 is directed to production of alkenediols by reaction of an alkenol with an aldehyde at a temperature from 235° to 400° C. (455° to 750° F.) and in the presence of a base selected from alkaline hydroxides, carbonates and bicarbonates, ammonia and hexamethylenetetramine. U.S. Pat. No. 3,574,773 is closely related to U.S. Pat. No. 3,692,848. U.S. Pat. No. 3,574,773 is directed to the reaction of an olefin with an aldehyde at a temperature from 235° to 400° C. and in the presence of a base such that the starting materials have a pH between 7 and 11, preferably 7.5 to 9. According to U.S. Pat. No. 3,574,773, the amount of base should be such that a sample of the reaction mixture after cooling has a pH value of from 6.5 to 10, preferably 7 to 9.

According to the examples in U.S. Pat. No. 3,692,848, 3-methylpentene-3-diol-1,5 is produced by reacting 3-methyl-3-buten-1-ol with formaldehyde in aqueous solution. U.S. Pat. No. 2,789,996 discloses the production of 3-methylene-1,5-pentanediol by reaction of 3-methyl-3-buten-1-ol with formaldehyde under anhydrous conditions and at a temperature between 200° and 350° C., and in the absence of a catalyst. Reaction pH conditions are not disclosed in U.S. Pat. No. 2,789,996, but it is stated that the reaction does not take place when the formaldehyde is in the form of aqueous formaldehyde.

SUMMARY OF THE INVENTION

We have found that in the production of alkenediols by the reaction of aqueous formaldehyde with an alkenemono-ol, it is important to maintain the pH below 7, preferably below 6.5, the contrary teaching of the first two above-mentioned patents notwithstanding. Specifically, we have surprisingly found that a pH between about 4 and 7, preferably above about 4 and below 6.5, results in optimum yields of the alkenediols, based on either of the reactants.

Thus, in accordance with the present invention, a process is provided for producing an alkenediol which comprises:

(a) contacting an alkenemono-ol feed in a reaction zone with a formaldehyde feed in aqueous medium;

(b) maintaining the pH in the reaction zone between about 4 and 7; and (c) maintaining reaction zone conditions sufficient to react the alkenemono-ol with the formaldehyde to yield alkenediol.

Frequently two or more isomeric alkenediols are produced by this reaction.

Suitable alkenol reactants include those described in U.S. Pat. No. 3,692,848.

The reaction which takes place, at a pH maintained between about 4 and 7 in accordance with the present invention, may be described as follows:

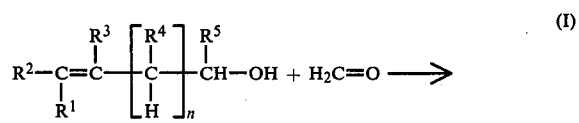

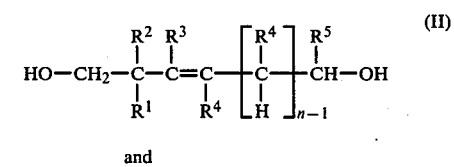

and

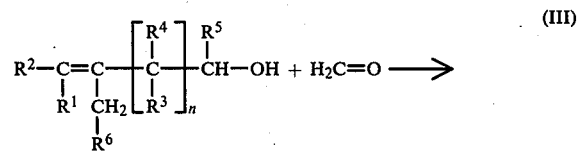

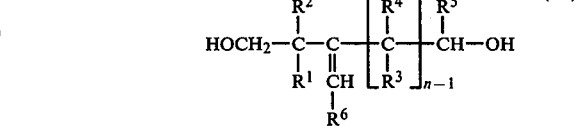

wherein $R^1$, $R^2$, $R^3$, $R^4$, $R^5$ and $R^6$ denote hydrogen atoms or hydrocarbon radicals having from 1 to 8 carbon atoms, and n denotes one of the integers from 1 to 12.

Preferred radicals $R^1$ to $R^6$, apart from hydrogen atoms, are alkyl groups having from 1 to 8 carbon atoms. Cycloalkyl groups having from 5- to 8-ring members, aralkyl groups such as the benzyl group, and aryl groups such as the phenyl or tolyl groups are also included.

Radicals $R^1$ to $R^5$ may also be joined together to form rings having from 5 to 12 members. A preferred compound having the formula (II) is 3-methyl-3-pentene-1,5-diol wherein $R^1$, $R^2$, $R^4$ and $R^5$ are hydrogen atoms, $R^3$ is methyl and n is 1. A preferred compound having the formula (IV) is 3-methylene-1,5-pentanediol wherein all the R groups are hydrogen atoms and n is 2.

Preferred compounds to be used as alkenols having the formula (I) are monounsaturated alkenols containing from 4 to 18, more preferably 5 to 8, carbon atoms, and either $R^3$ or both $R^1$ and $R^2$ are alkyl groups; for example, compounds having the formulas as given below:

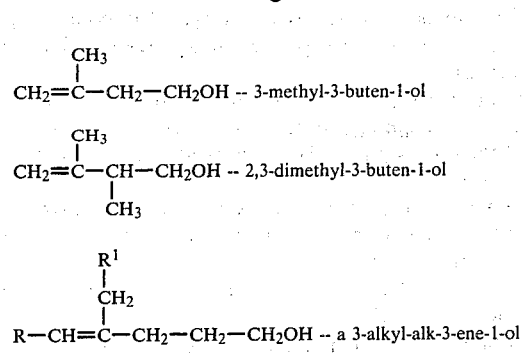

$$CH_2=\overset{\overset{\displaystyle CH_3}{|}}{C}-CH_2-CH_2OH \text{ -- 3-methyl-3-buten-1-ol}$$

$$CH_2=\overset{\overset{\displaystyle CH_3}{|}}{C}-\overset{\overset{\displaystyle |}{CH}}{\underset{\underset{\displaystyle CH_3}{|}}{}}-CH_2OH \text{ -- 2,3-dimethyl-3-buten-1-ol}$$

$$R-CH=\overset{\overset{\displaystyle R^1}{|}}{\underset{\underset{\displaystyle CH_2}{|}}{C}}-CH_2-CH_2-CH_2OH \text{ -- a 3-alkyl-alk-3-ene-1-ol}$$

Alkenols to be used as starting materials may be prepapred in various known ways.

Solvents may be used to promote (or enhance) the miscibility of the alkenol and the aqueous formaldehyde, and are especially desirable if the alkenol contains 6 or more carbon atoms. Particularly useful solvents are the lower alcohols, alcohol-ethers, and cyclic ethers such as methyl, ethyl, propyl, isopropyl and isobutyl alcohols, 1,4-dioxane, tetrahydrofuran and 2-ethoxyethanol. The lower alcohols are preferred.

If the alkenol used as a starting material is derived from the reaction of olefins and formaldehyde, it may be convenient to add the starting olefin to the reaction mixture of alkenol and formaldehyde, or of alkenol, formaldehyde and solvent. In this way, some or all of the desired alkenol may be made simultaneously with the diols. Further in this regard, see our commonly assigned application, Ser. No. 379,511.

The pH in the reaction zone can be monitored or adjusted by controlling the pH of the formaldehyde or formaldehyde-water solution added to the reaction zone, but other methods can also be employed for pH control. Within the spirit of the present invention, the pH may be slightly outside the range of 4 to 7 at the start of the reaction, particularly due to solvent effects, but the pH must be maintained between about 4 and 7 during the main course of the reaction. The term "pH" is used herein to mean the pH as measured at room temperature (60° to 80° F.), even though the reaction is carried out at elevated temperature. Among other reasons, this is because there is difficulty in obtaining reproducible and accurate pH measurements at elevated temperature.

The reaction is carried out in the presence of at least 5% water, based on the aldehyde and water, for example 5 to 90 weight percent water, and more preferably 20 to 80 weight percent water, based on the combined aldehyde and water fed to the reaction zone.

The desired pH in the process of the present invention is preferably maintained by the use of a buffer. The term "buffer" is used herein in its ordinary chemical sense to mean a substance which when added to a solution resists a change in hydrogen-ion concentration on addition or formation of acid or alkali. Preferred buffering agents for use in the process of the present invention comprise a weak acid and (i.e., together with) a salt of a weak acid. Preferably the buffers are mixtures of polybasic acids and salts of polybasic acids. Mixtures of weak acids or partial salts of weak acids and weak bases may also be used. The term "weak acid" is used herein to mean those acids which have a pka larger than 2.8.

The acids and salts of the acids may be added as such, or the desired mixture may be prepared by partially neutralizing a weak acid with a base such as sodium hydroxide or potassium carbonate. The materials composing the buffer should be reasonably stable in the reaction mixture at reaction conditions.

Examples of buffering agents which we have found to be advantageous in the process of the present invention include a lower carboxylic acid and sodium or potassium hydrogen phosphate; sodium dihydrogen phosphate and sodium hydrogen phosphate; potassium dihydrogen phosphate and potassium hydrogen phosphate. The term "lower carboxylic acid" is used herein to mean a 1- to 6-carbon-atom carboxylic acid.

The buffers which we have found to be the most preferred are: (1) citric acid and disodium hydrogen phosphate; (2) diglycolic acid and disodium hydrogen phosphate; and (3) succinic acid and disodium succinate.

The amount of buffering agent added as a weak acid plus a salt of a weak acid is preferably 0.1 to 2, more preferably 0.5 to 1.6 weight percent, based on the combined total of formaldehyde and water fed to the reaction zone. The formaldehyde-water solution fed to the reaction zone, as a combined formaldehyde water feed or as a separate formaldehyde and a separate water feed, contains 5 to 90 weight percent water. Formalin is a preferred formaldehyde-water mixture for use in the present invention. Formalin is about 25 to 50 weight percent formaldehyde in water.

We have found that preferred reaction zone temperatures in the process of the present invention are about 300° to 600° F., more preferably 350° to 500° F., and most preferably 350° to 450° F. Preferably the reaction mixture is kept below its critical temperature, so that it can be maintained in true liquid phase.

Pressures used in the reaction zone in the process of the present invention preferably are sufficient to maintain substantial liquid phase. Pressures of 50 psig to 3000 psig can be used, and 100 to 1500 psig is preferred.

Thus, according to a preferred embodiment of the present invention, a process is provided for producing an alkenediol which comprises:

(a) contacting a straight- or alkyl branched-chain mono-unsaturated alkenol which has 5 to 18, preferably 5 to 8, carbon atoms with a formaldehyde-water solution containing 5 to 90 weight percent water, in a reaction zone at a temperature between about 350° and 500° F. and a pressure sufficient to maintain substantial liquid-phase reaction conditions; and (b) adding to the reaction zone 0.1 to 2 weight percent, based on the formaldehyde-water solution, of a buffering agent comprising a weak acid and the salt of a weak acid, to thereby maintain the pH between about 4 and 7 in the reaction zone.

BRIEF DESCRIPTION OF THE DRAWING

The drawing is a graph illustrating the dramatic effect which we have found is exerted on the yield of alkenediol from the reaction of alkenol with formaldehyde when maintaining the pH between about 4 and 7 in accordance with the present invention.

FURTHER DESCRIPTION OF THE DRAWING AND EXAMPLES

Referring now in more detail to the drawing and the exemplary runs which are graphically presented by the drawing, the ordinate represents the mol percent yield of hexenediols from the reaction of 3-methyl-3-buten-1-ol and formalin; and the abscissa of the drawing represents the initial pH of the aqueous formaldehyde solution fed to the reaction zone. The results of the following exemplary runs are graphically presented in the drawing.

EXAMPLE 1

Effect of pH in reaction of 3-methyl-3-buten-1-ol with formaldehyde (a) A microbomb of 14-ml capacity was charged with 4.8 g (0.056 mol) of 3-methyl-3-buten-1-ol and 2.2 g of a formalin solution made of of 35.6% formaldehyde (0.06 mol), about 50% water and about 11% methanol. A mixture of 0.0054 g of disodium hydrogen phosphate and 0.0040 g of citric acid monohydrate was added along with the formalin. The initial pH of the reactants was 4.9.

The reactor was rapidly heated to 400° F. and agitated at that temperature for 60 minutes. It was then cooled to ambient temperature, and the pH of the reaction mixture was found to be 5.4. Analysis by vapor-phase chromatography using 2-ethylhexanol as the internal standard showed the reaction mixture to contain 40.6% (weight) of 3-methyl-3-buten-1-ol, 20.5% of an essentially equimolar mixture of 3-methylene-1,5-pentanediol and 3-methyl-2-pentens-1,5-diol, and 6.9% higher-boiling material. Using these values, the mixed hexenediol yield was calculated to be 47% based on formaldehyde charged (100% conversion basis) and 58% based on 3-methyl-3-buten-1-ol converted.

(b) The same experiment was repeated, except that the buffer was made up of 0.006 g of disodium hydrogen phosphate and 0.004 g of citric acid monohydrate, giving an initial pH of 5.3 and a final pH of 5.3. Analysis showed a 59% yield of mixed hexenediols based on 3-methyl-3-buten-1-ol converted and 47% based on formaldehyde charged.

(c) The same experiment was repeated, except that the buffer was made up of 0.007 g of disodium hydrogen phosphate and 0.003 g of citric acid monohydrate. The initial pH was 6.1, and the final pH was 5.3. Analysis showed a 58% yield of mixed hexenediols based on 3-methyl-3-buten-1-ol converted and a 46% yield based on formaldehyde charged.

(d) The same experiment was carried out without a buffer. The initial pH was 3.6 and the final pH was 3.5. Yields of hexenediols were determined as before, and were found to be 14% based on 3-methyl-3-buten-1-ol and 16% based on formaldehyde.

(e,f) The same experiment was repeated twice more utilizing the same disodium hydrogen phosphate/citric acid monohydrate buffer in a ratio to give an initial pH of 7.8 and 9.7. After reaction at 400° F., the final pH was 5.0 and 4.9, respectively. Yields of hexenediols based on 3-methyl-3-buten-1-ol converted were 57% and 50%, respectively, and yields based on formaldehyde charged were 40% and 26%, respectively.

These results are plotted on the drawing, and show that higher yields are obtained when the pH is maintained in the range 4 to 7.

EXAMPLE 2

Effect of reaction time on yield (a) Three 14-ml microbombs were each charged with 4.75 g (0.0475 mol) of 2,3-dimethyl-3-buten-1-ol and 2.2 g of 37% aqueous formalin (0.0271 mol formaldehyde) solution containing 0.16 g of disodium hydrogen phosphate and 0.011 g of citric acid monohydrate. The reactors were agitated and heated to 392° F. At various times, the contents of the reactors were removed and the products analyzed by vapor-phase chromatography as in Example 1. Yields of mixed heptenediols were determined by the procedure used in Example 1, and are as follows:

| | Yield of Heptenediols, % based on | |
|---|---|---|
| Time (min.) | Formaldehyde charged | 2,3-Dimethyl-3-buten-1-ol converted |
| 30 | 22 | 40 |
| 60 | 32 | 52 |
| 90 (from Plot) | — | 50 |
| 120 | 35 | 44 |

(b) The same experiment was carried out using potassium dihydrogen phosphate as the buffer. The results were as follows:

| | Yield of Heptenediols, % based on | |
|---|---|---|
| Time (min.) | Formaldehyde charged | 2,3-Dimethyl-3-buten-1-ol converted |
| 30 | 20 | 37 |
| 60 | 28 | 40 |
| 90 | 25 | 30 |

(c) The same experiment was carried out without any buffer or other pH control. The results were as follows:

| | Yield of Heptenediols, % based on | |
|---|---|---|
| Time (min.) | Formaldehyde charged | 2,3-Dimethyl-3-buten-1-ol converted |
| 30 | 19 | 25 |
| 60 | 24 | 29 |
| 90 | 15 | 13 |

These experiments illustrate the advantages realized by carrying out the unsaturated alcohol/formaldehyde reaction in the presence of a buffer.

EXAMPLE 3

Buffered by mixed phosphate salts (a) A 14-ml microbomb was charged with 1.9 g (0.0221 mol) of 3-methyl-3-buten-1-ol, 0.32 g (0.01 mol) of paraformaldehyde, 0.39 g of a standard (Coleman Instruments Company) disodium hydrogen phosphate and potassium dihydrogen phosphate, pH=7, buffer solution, and 0.1 g of methanol. The bomb was sealed, placed in a heater block at 392° F., and agitated at that temperature for 2 hours. After cooling to room temperature, the reaction product was analyzed by vapor-phase chromatography. The results are shown below.

(b) The same reaction as in 3(a) was carried out using 0.39 g of distilled water in place of the buffer solution. The results are shown below, all values being in area percent.

| | (a) | (b) |
|---|---|---|
| Low-boiling compounds | 17.5 | 19.0 |
| 3-methyl-3-buten-1-ol | 57.6 | 40.0 |
| Intermediates | 1.0 | 4.8 |
| 3-methylene-1,5-pentanediol | 7.5 | 4.3 |
| 3-methyl-3-pentene-1,5-diol | 5.9 | 0.9 |
| Higher-boiling compounds | 10.5 | 31.0 |

From these results, it can be concluded that the presence of a buffer resulted in: (1) higher yields of the desired diol mixture (13.4 vs. 5.2); (2) considerably less decomposition of the 3-methyl-3-pentene-1,5-diol (ratio of 3-methylene-1,5-pentanediol to 3-methyl-3-pentene-1,5-diol 1.27:1 vs. 4.8:1) and (3) much less by-product formation (intermediates+high-boiling compounds, 11.5 vs. 35.8).

(c) Another run was carried out using the same procedure as in Example 3(a), except that 0.39 g of a standard (Coleman Instruments Company) potassium hydrogen phthalate, pH=4.01, buffer solution in place of the pH=7.0 buffer solution. The results were essentially the same as in Example 3(a).

EXAMPLE 4

Reactions of other unsaturated alcohols with formaldehyde in the presence of buffers (a) A 14-ml microbomb was charged with 2.8 g (0.0197 mol) of 3-methylene-5,5-dimethyl-1-hexanol, 2.8 g of 2-propanol, 1.6 g of an aqueous buffered formaldehyde (0.028 mol formaldehyde) solution (said solution was prepared by mixing 1100 g of 37% aqueous formalin, 6.1 g of disodium hydrogen phosphate, and 2.3 g of diglycolic acid). The initial pH was 6.1. The microbomb was shaken at a temperature of 420° F. for 2 hours. At the end of this time, the pH was 5.3. Analysis showed the product to contain appreciable quantities of 3-neopentyl-2-pentene-1,5-diol as well as unconverted starting material, the ratio of diol product to mono-ol starting material being 0.23:1.

(b) A 14-ml microbomb was charged with 4.0 g (0.027 mol) of 3-phenyl-3-buten-1-ol, 2.0 g of 2-propanol, and 1.3 g of an aqueous buffered formaldehyde solution (said solution was prepared by dissolving 0.70 g of disodium hydrogen phosphate and 0.30 g of citric acid monohydrate in 80 ml of 36% formalin). The initial pH was 6.15. The resulting mixture was shaken and heated at 410° F. for 1 hour. At the end of this time, the pH was 5.5. Analysis gave the following distribution of materials in the reaction product:

84.3 parts of 3-phenyl-3-buten-1-ol
6.3 parts of intermediate compounds
4.3 parts of 3-phenyl-2-pentene-1,5-diol
0.5 part of high-boiling compounds

EXAMPLE 5

Phthalate Buffer

A 14-ml microbomb was charged with 4.8 g (0.056 mol) of 3-methyl-3-buten-1-ol and 2.2 g of an aqueous formaldehyde solution (said solution was prepared by dissolving 0.40 g of potassium hydrogen phthalate and 0.87 g of sodium carbonate in 100 ml of 37% formalin). The resulting pH was 5.6. The reaction mixture was shaken and heated at 400° F. for 1 hour. At the end of this time, the pH was 5.1. Analysis by the method of Example 1(a) showed the yield of mixed hexenediols to be 85% and 60% as based on 3-methyl-3-buten-1-ol and formaldehyde, respectively.

(b) A 5-gal autoclave was charged with 6200 g (73 mols) of aqueous 37% formalin solution, 296 g of an aqueous solution containing 59.2 g of sodium hydrogen succinate. The initial pH was 5.1. The autoclave was sealed and heated to 310° F. A pressure of 100 psig was maintained throughout the run. Samples were removed hourly and analyzed. The pH of each sample was in the range 4.9 to 5.0. At the end of 8 hours, the run was terminated. Analysis showed a 50% conversion of 3-methyl-3-buten-1-ol and a 60% conversion of formaldehyde. Yields of the mixed hexenediols were 74% and 62%, based on 3-methyl-3-buten-1-ol and formaldehyde converted, respectively.

EXAMPLE 6

Effect of pH on the reaction of 3-methyl-3-buten-1-ol with formaldehyde in the presence of ammonia (a) Microbombs of b 14-ml capacity were charged with 4.8 g (0.056 mol) of 3-methyl-3-buten-1-ol and 2.2 g of an aqueous solution prepared from 0.00132 g of ammonia, 0.042 g of formic acid, and 0.7832 g (0.025 mol) of formaldehyde. The initial pH was 5.2. These bombs were shaken and heated at 205° C. for 30, 60 and 90 minutes, respectively. At the end of these times, the contents were analyzed, and yields were calculated by the methods of Example 1. The results are given in Table I, and the results of the 60-minute run are plotted in the drawing in terms of the initial pH of the above-mentioned aqueous formaldehyde solution.

(b,c,d,e) Other runs were carried out as described above, except that the quantity of ammonia was increased to 0.00264 g (b): to 0.0066 g (c); to 0.0132 g (d); and to 0.0264 g (e). The initial pH values were 6.25 (b); 6.8 (c); 7.35 (d); and 7.4 (e). The results are given in Table I, and the results of the 60-minute run are plotted in the drawing.

(f) Example 6(a) was repeated except that no ammonia was present and the reaction time was 60 minutes. The initial pH was 3.6. The results are given in Table I.

(g,h) Example 6(c) was repeated, except that the temperature was 238° C. (g) and 260° C. (h). The results are given in Table I.

TABLE I

REACTION OF 3-METHYL-3-BUTEN-1-OL WITH FORMALDEHYDE IN THE PRESENCE OF AMMONIA

| Run No. | Reaction Time, minutes | Final pH | Mixed Hexenediol Yields, Mol % Based on | |
|---|---|---|---|---|
| | | | 3-Methyl-3-buten-1-ol Converted | Formaldehyde Charged |
| 6a | 30 | 4.6 | 56 | 37 |
| | 60 | 4.8 | 61 | 46 |
| | 90 | 4.9 | 55 | 49 |
| 6b | 30 | 5.3 | 65 | 38 |
| | 60 | 5.6 | 69 | 48 |
| 6c | 30 | 6.95 | 86 | 38 |
| | 60 | 5.5 | 63 | 42 |
| | 120 | 5.5 | 68 | 36 |
| 6d | 30 | 5.75 | 55 | 28 |
| | 60 | 5.75 | 50 | 30 |
| 6e | 30 | 5.8 | 41 | 19 |
| | 60 | 6.4 | 49 | 22 |
| 6f | 60 | 3.5 | 14 | 16 |
| 6g | 10 | 5.1 | 62 | 41 |
| | 30 | 5.9 | 55 | 46 |
| | 60 | 6.4 | 34 | 36 |
| 6h | 10 | 5.4 | 45 | 42 |
| | 30 | 6.5 | 29 | 36 |
| | 60 | 6.9 | 19 | 28 |

What is claimed is:

1. A process for producing an alkenediol which comprises:
   (a) feeding an alkenemono-ol to a reaction zone and therein contacting the alkenemono-ol with a formaldehyde feed in an aqueous medium; and
   (b) maintaining the pH in the reaction zone above about 4 and below 6.5, the temperature between 300° and 600° F., and the pressure sufficient to maintain liquid phase, thereby reacting the alkenol with the formaldehyde to yield alkenediol.

2. A process in accordance with claim 1 wherein the reaction is carried out in the presence of at least 5 weight percent water based on the formaldehyde and water.

3. A process in accordance with claim 2 wherein the alkenemono-ol has 4 to 18 carbon atoms.

4. A process in accordance with claim 3 wherein the pH is maintained by the use of a buffer.

5. A process in accordance with claim 4 wherein the buffer comprises a weak acid and a salt of a weak acid.

6. A process in accordance with claim 5 wherein the buffer is a lower polycarboxylic acid and disodium or dipotassium hydrogen phosphate; or potassium dihydrogen phosphate and potassium hydrogen phosphate; or sodium dihydrogen phosphate and disodium hydrogen phosphate.

7. A process in accordance with claim 5 wherein the alkenol is a straight- or alkyl branched-chain monounsaturated alkenemono-ol having 5 to 8 carbon atoms.

8. A process in accordance with claim 7 wherein the alkenenemono-ol is 3-methyl-3-buten-1-ol or 2,3-dimethyl-3-buten-1-ol.

9. A process for producing an alkenediol which comprises:

(a) feeding a straight- or alkyl branched-chain mono-unsaturated alkenemono-ol which has 5 to 8 carbon atoms to a reaction zone and therein contacting the mono-ol with a formaldehyde-water solution containing 5 to 90 weight percent water, at a temperature between about 350° and 500° F. and a pressure sufficient to maintain substantial liquid-phase reaction conditions; and (b) adding to the reaction zone 0.1 to 2 weight percent, based on the formaldehyde-water solution, of a buffering agent comprising a weak acid and the salt of a weak acid, to thereby maintain the pH above about 4 and below 6.5 in the reaction zone, thereby reacting the mono-ol with the formaldehyde to yield an alkenediol which has 6 to 9 carbon atoms.

* * * * *